United States Patent

Obata et al.

Patent Number: 5,221,685
Date of Patent: Jun. 22, 1993

[54] THIAZOLINE DERIVATIVE, PROCESS FOR PREPARING THE SAME AND CHEMICAL FOR CONTROLLING NOXIOUS ORGANISMS CONTAINING THE SAME

[75] Inventors: Tokio Obata; Katsutoshi Fujii; Yasuhisa Fukuda; Kiyoshi Tsutsumiuchi; Yoshinori Yamanaka, all of Ube, Japan

[73] Assignee: UBE Industries, Ltd., Yamaguchi, Japan

[21] Appl. No.: 828,110

[22] Filed: Jan. 30, 1992

[30] Foreign Application Priority Data

Feb. 1, 1991 [JP] Japan .................................. 3-98364
Jul. 9, 1991 [JP] Japan ................................ 3-263308
Aug. 30, 1991 [JP] Japan ................................ 3-298588

[51] Int. Cl.$^5$ ................. C07D 277/46; C07D 277/48; A01N 43/78
[52] U.S. Cl. .................................. 514/371; 548/195; 548/196
[58] Field of Search ................. 548/195, 196; 514/371

[56] References Cited

U.S. PATENT DOCUMENTS 4,249,012 2/1981 Crossley ............................ 548/195

FOREIGN PATENT DOCUMENTS 57371 4/1983 Japan .
1131207 10/1968 United Kingdom .

OTHER PUBLICATIONS

Mar., Advanced Organic Chemistry p. 794, 1985.

Primary Examiner—Robert Gerstl
Attorney, Agent, or Firm—Finnegan, Henderson, Farabow, Garrett & Dunner

[57] ABSTRACT

Disclosed are a thiazoline compound represented by the following formula (I):

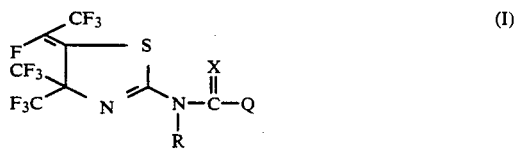

wherein R represents hydrogen atom or a lower alkyl group, X represents oxygen atom or sulfur atom, and Q represents Ar (where Ar represents a substituted or unsubstituted phenyl group or a substituted or unsubstituted naphthyl group) or

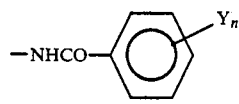

(where Y represents a halogen atom, a lower alkyl group, a lower alkoxy group, a lower haloalkyl group, a lower haloalkoxy group, nitro group, acetyl group or cyano group and n represents an integer of 0 to 5), a process for preparing the same and a chemical for controlling noxious organisms containing the same as an active ingredient.

14 Claims, No Drawings

THIAZOLINE DERIVATIVE, PROCESS FOR PREPARING THE SAME AND CHEMICAL FOR CONTROLLING NOXIOUS ORGANISMS CONTAINING THE SAME

BACKGROUND OF THE INVENTION

This invention relates to a novel thiazoline derivative such as 2-acylamino-2-thiazoline derivative or 1-(thiazolin-2-yl)-3-benzoylurea derivative which is available as a chemical for controlling noxious organisms and a process for preparing the same.

As a similar compound in structure to 2-acylamino-2-thiazoline derivative of the present invention, 2-acetamido-4,4-bis(trifluoromethyl)-5-tetrafluoroethylidene)-thiazoline has been described in Japanese Provisional Patent Publication No. 57371/1985. However, in the above publication, there is no description about the use as an agricultural agent or biological test of the compound.

The thiazoline derivatives such as 2-acylamino-2-thiazoline derivative or 1-(thiazolin-2-yl)-3-benzoylurea derivative of the present invention are novel compounds, and thus their activities of controlling noxious organisms have been not known.

SUMMARY OF THE INVENTION

An object of the present invention is to provide a novel thiazoline derivative such as 2-acylamino-2-thiazoline derivative or 1-(thiazolin-2-yl)-3-benzoylurea derivative, a process for preparing the same and a chemical for controlling noxious organisms containing the same as an effective ingredient.

The present inventors have studied intensively in order to solve the above problems, and consequently found that a novel thiazoline derivative has remarkable activity of controlling noxious organisms, to accomplish the present invention.

That is, the present invention is concerned to a thiazoline derivative represented by the following formula (I):

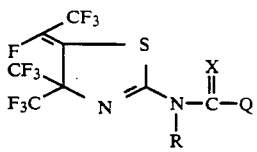 (I)

wherein R represents hydrogen atom or a lower alkyl group, X represents oxygen atom or sulfur atom, and Q represents Ar (where Ar represents a phenyl group which may be substituted by 1 to 5 substituents selected from the group consisting of a halogen atom, a lower alkoxy group, a lower alkyl group, nitro group, a lower haloalkyl group, cyano group, a phenyloxy group which may be substituted by a halogen atom, an aralkyloxy group which may be substituted by a halogen atom, a lower alkylamino group, hydroxyl group, carboxyl group, a lower haloalkoxy group, a lower alkylsulfonyl group, a lower alkylthio group and methylenedioxy group, or a naphthyl group which may have a substituent) or

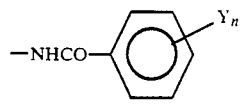

(where Y represents a halogen atom, a lower alkyl group, a lower alkoxy group, a lower haloalkyl group, a lower haloalkoxy group, nitro group, acetyl group or cyano group, n represents an integer of 0 to 5 and when n=2, $Y_n$ represents an unsaturated 6-membered ring formed with carbon atoms to which Y's are bonded and fused to the benzene ring,
provided that Q is

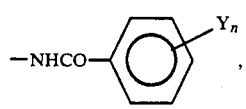,

R is hydrogen atom and X is oxygen atom).

The second invention relates to a process for preparing a 2-acylamino-2-thiazoline derivative represented by the formula (I-a):

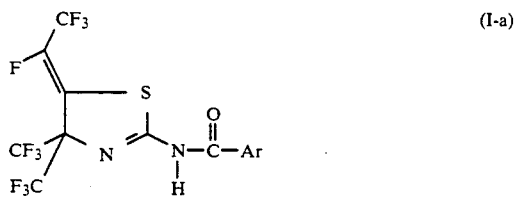 (I-a)

wherein Ar represents a phenyl group which may be substituted by 1 to 5 substituents selected from the group consisting of a halogen atom, a lower alkoxy group, a lower alkyl group, nitro group, a lower haloalkyl group, cyano group, a phenyloxy group which may be substituted by a halogen atom, an aralkyloxy group which may be substituted by a halogen atom, a lower alkylamino group, hydroxyl group, carboxyl group, a lower haloalkoxy group, a lower alkylsulfonyl group, a lower alkylthio group and methylenedioxy group, or a naphthyl group which may have a substituent,
among the compound represented by the above formula (I) which comprises reacting a 2-iminothiazolidine derivative represented by the following formula (II):

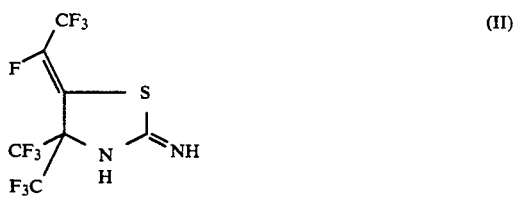 (II)

with a benzoic acid derivative represented by the following formula (III) or a reactive derivative thereof:

Ar—COOH (III)

wherein Ar has the same meaning as defined above.

The third invention relates to a process for preparing a 2-amino-2-thiazoline derivative (I-b) represented by the following formula:

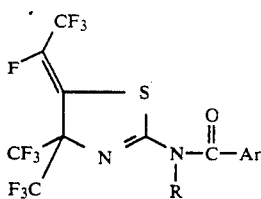
(I-b)

wherein Ar and R each have the same meanings as defined above,
among the compound represented by the above formula (I) which comprises reacting a 2-amino-2-thiazoline derivative represented by the following formula (IV):

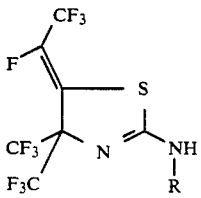
(IV)

wherein R has the same meaning as defined above, with the benzoic acid derivative represented by the above formula (III) or the reactive derivative thereof. The fourth invention relates to a process for preparing a 2-thioacylamino-2-thiazoline derivative represented by the following formula (I-c):

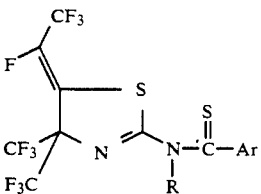
(I-c)

wherein Ar and R have the same meanings as defined above,
among the compound represented by the above formula (I) which comprises subjecting the above compound (I-a) or the above 2-acylamino-2-thiazoline derivative represented by the above formula (I-b) to thiocarbonylation.

The fifth invention relates to a process for preparing a 1-(thiazolin-2-yl)-3-benzoylurea derivative represented by the formula (I-d):

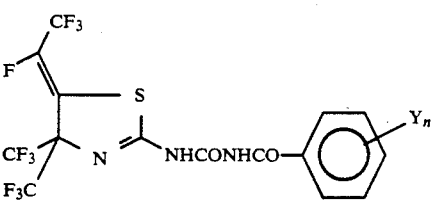
(I-d)

wherein Y and n have the same meaning as defined above, among the compound represented by the above formula (I) which comprises reacting the iminothiazolidine derivative represented by the above formula (II) with a benzoylisocyanate derivative represented by the following formula:

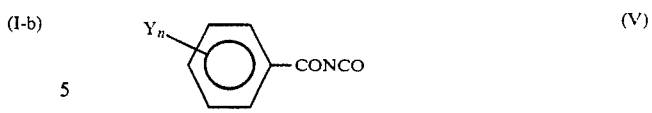
(V)

wherein Y and n have the same meanings as defined above.

The sixth invention relates to a chemical for controlling noxious organisms containing the thiazoline derivative represented by the above formula (I) as an effective ingredient.

DESCRIPTION OF THE PREFERRED EMBODIMENTS

In the following, the present invention will be explained in detail.

In the present invention, preferred thiazoline derivatives are as shown below.

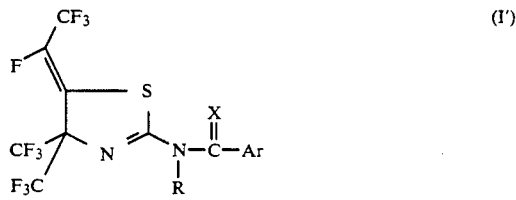
(I')

wherein R represents hydrogen atom or a lower alkyl group, X represents oxygen atom or sulfur atom, and Ar represents a phenyl group which may be substituted by 1 to 5 substituents selected from the group consisting of a halogen atom, a lower alkoxy group, a lower alkyl group, nitro group, a lower haloalkyl group, cyano group, a phenyloxy group which may be substituted by a halogen atom, an aralkyloxy group which may be substituted by a halogen atom, a lower alkylamino group, hydroxyl group, carboxyl group, a lower haloalkoxy group, a lower alkylsulfonyl group, a lower alkylthio group and methylenedioxy group, or a naphthyl group which may have a substituent.

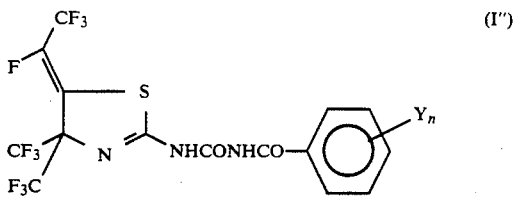
(I")

wherein Y represents a halogen atom, a lower alkyl group, a lower alkoxy group, a lower haloalkyl group, a lower haloalkoxy group, nitro group, acetyl group or cyano group, n represents an integer of 0 to 5 and when n=2, $Y_n$ represents an unsaturated 6-membered ring formed with carbon atoms to which Y's are bonded and fused to the benzene ring.

In the novel thiazoline derivative (I) ((I') or (I")) which is the above desired compound, and the compounds (II) to (V) which are the starting materials thereof), as Ar of Q, there may be mentioned a phenyl group or a naphthyl group each of which may have a substituent. As the substituent, there may be mentioned a halogen atom, a lower alkoxy group, a lower alkyl group, nitro group, a lower haloalkyl group, cyano group, a phenyloxy group which may be substituted by a halogen atom, an aralkyloxy group which may be substituted by a halogen atom, a lower alkylamino group, hydroxyl group, carboxyl group, a lower haloalkoxy group, a lower alkylsulfonyl group, a lower alkylthio group, methylenedioxy group.

Preferred substituents for Ar are as follows.

Among the halogen atom (e.g. chlorine atom, iodine atom, bromine atom and fluorine atom), chlorine atom, bromine atom and fluorine atom are preferred.

As the lower alkoxy group, those having 1 to 6 carbon atoms are preferred, more preferably a straight or branched one having 1 to 4 carbon atoms, and particularly preferably methoxy group.

As the lower alkyl group, those having 1 to 6 carbon atoms are preferred, more preferably a straight or branched one having 1 to 4 carbon atoms.

As the lower haloalkyl group (e.g. a straight or branched one having 1 to 6 carbon atoms having a halogen atom such as chlorine atom, iodine atom, bromine atom and fluorine atom), a straight or branched one having 1 to 4 carbon atoms is preferred, and more preferably trifluoromethyl group.

As the phenyloxy group which may be substituted by a halogen atom (e.g. chlorine atom, iodine atom, bromine atom and fluorine atom), 4-fluorophenoxy group and phenoxy group are preferred.

As the aralkyloxy group which may be substituted by a halogen atom (e.g. chlorine atom, iodine atom, bromine atom and fluorine atom), benzyloxy group, phenethyloxy group and phenylpropyloxy group are preferred and benzyloxy group is more preferred.

As the lower alkylamino group (e.g. a straight or branched one having 1 to 6 carbon atoms), a straight or branched one having 1 to 4 carbon atoms is preferred, and more preferably dimethylamino group.

As the lower haloalkoxy group (e.g. a straight or branched one having 1 to 6 carbon atoms having a halogen atom such as chlorine atom, iodine atom, bromine atom and fluorine atom), a straight or branched one having 1 to 4 carbon atoms is preferred, and more preferably trifluoromethoxy group, 2-chloro-1,1,2-trifluoroethoxy group.

As the lower alkylsulfonyl group (e.g. a straight or branched one having 1 to 6 carbon atoms), a straight or branched one having 1 to 4 carbon atoms is preferred, and more preferably methanesulfonyl group.

As the lower alkylthio group (e.g. a straight or branched one having 1 to 6 carbon atoms), a straight or branched one having 1 to 4 carbon atoms is preferred, and more preferably methylthio group.

As the number of the substituent, an integer of 1 to 5 may be mentioned and the position(s) of the substituent(s) is/are not limited, but preferred number and the position thereof are as follows.

The halogen atom is 2, 3, 4, 5 and/or 6-position.
The lower alkoxy group is 3-position.
The lower alkyl group is 4-position.
The nitro group is 3, 4 and/or 5-position.
The lower haloalkyl group is 3, 4 and/or 5-position.
The cyano group is 4-position.
The phenyloxy group which may be substituted by a halogen atom is 3 and/or 4-position.
The aralkyloxy group which may be substituted by a halogen atom is 3 -position.
The lower alkylamino group is 3-position.
The hydroxyl group is 3-position.
The carboxyl group is 6-position.
The lower haloalkoxy group is 4 and/or 5-position.

The lower alkylsulfonyl group is 4-position.
The lower alkylthio group is 4-position.

As the reactive derivative of the benzoic acid derivative represented by the formula (III) which is a starting compound to be used for producing the compound (I) of the present invention, there may be mentioned, for example, an acid anhydride, acid chloride or acid bromide of a carboxylic acid corresponding to the benzoic acid derivative, or a carboxylate (e.g. methyl carboxylate, ethyl carboxylate, phenyl carboxylate), but preferably an acid anhydride or acid chloride of a carboxylic acid.

As the R, hydrogen atom or methyl group is preferred.

As the X, oxygen atom and sulfur atom may be mentioned.

As the Y, there may be mentioned a halogen atom, a lower alkyl group, a lower alkoxy group, a lower haloalkyl group, a lower haloalkoxy group, nitro group, acetyl group or cyano group. As the halogen atom (e.g. chlorine atom, iodine atom, bromine atom and fluorine atom), chlorine atom, bromine atom and fluorine atom are preferred. As the lower alkyl group (e.g. those having 1 to 6 carbon atoms), a straight or branched one having 1 to 4 carbon atoms is preferred, and more preferably methyl group. As the lower alkoxy group (e.g. those having 1 to 6 carbon atoms), a straight or branched one having 1 to 4 carbon atoms is preferred, and more preferably methoxy group. As the lower haloalkyl group (e.g. a straight or branched one having 1 to 6 carbon atoms having a halogen atom such as chlorine atom, iodine atom, bromine atom and fluorine atom), a straight or branched one having 1 to 4 carbon atoms is preferred, and more preferably trifluoromethyl group. As the lower haloalkoxy group (e.g. a straight or branched one having 1 to 6 carbon atoms having a halogen atom such as chlorine atom, iodine atom, bromine atom and fluorine atom), a straight or branched one having 1 to 4 carbon atoms is preferred, and more preferably trifluoromethoxy group.

As the n, an integer of 0 to 5 may be mentioned, but preferably 1 or 2.

The position of $Y_n$ is/are not specifically limited, but preferably 2- or 4-position.

When n=2, Y's may form an unsaturated 6-membered ring fused to the benzene ring with carbon atoms to which Y's are bonded, and preferably form o-naphthyl group or β-naphthyl group with the benzene ring.

The compound (I) of the present invention can be prepared, for example, according to the preparation methods 1 to 4 as mentioned below.

SYNTHETIC METHOD 1

Synthesis of the compound (I-a) of the present invention can be carried out by reacting the starting compound (II) and the compound (III) in a solvent in the presence of a reaction aid as shown below.

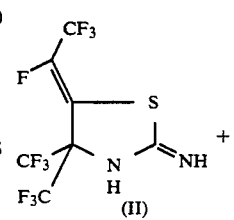

Benzoic acid derivative or its reactive derivative —Reaction aid→

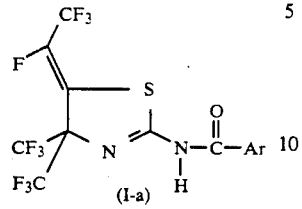
(I-a)

wherein Ar has the same meaning as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloromethane, dichloroethane, trichloroethylene and cyclohexane; ethers such as diethyl ether, tetrahydrofuran and dioxane; ketones such as acetone and methyl ethyl ketone; alcohols such as methanol, ethanol and ethylene glycol or hydrates thereof; amides such as N,N-dimethylformamide and N,N-dimethylacetamide; organic bases such as triethylamine, pyridine and N,N-dimethylaniline; 1,3-dimethyl-2-imidazolidinone; dimethyl sulfoxide; and a mixture of the above solvents.

The solvent may be used such an amount that a concentration of the compound (II) is in the range of 5 to 80% by weight, but preferably such an amount that the concentration of the compound (II) is in the range of 10 to 70% by weight.

As the reaction aid, there may be mentioned a base (e.g. organic bases such as triethylamine, pyridine, 4-(N,N-dimethylamino)pyridine and N,N-dimethylaniline; alkali metal alkoxides such as sodium methoxide and sodium ethoxide; and inorganic bases such as sodium amide, sodium hydroxide, potassium hydroxide, potassium carbonate, sodium carbonate and sodium hydride), a dehydrating agent (e.g. dicyclohexylcarbodiimide, 1-ethyl-8-(8-dimethylaminopropyl)carbodiimide hydrochloride, 1,1-carbodiimidazole, phosphorus pentachloride, phosphorus trichloride, phosphorus oxychloride, thionyl chloride and phosgene), and the like.

The reaction aid may be used in an amount of 0.001 to 5-fold mole per mole of the compound (II).

The reaction temperature is not particularly limited, but it is generally carried out in the temperature range of from room temperature to a boiling point or lower of a solvent used.

The reaction time varies depending on the above concentration of the starting material and the temperature, but may be generally 0.3 to 24 hours.

The starting compound (III) may be used in an amount of 0.5 to 2-fold mole based on the mole of the starting compound (II), but preferably 0.8 to 1.5-fold mole.

The compound (II) to be used in the present invention can be easily produced by using perfluoro-(2-methyl-2-pentene), etc. and thiourea according to the method described in, for example, Japanese Provisional Patent Publication No. 57371/1983, etc.

The reactive derivative of the carboxylic acid (III) to be used in the present invention can be produced, when it is an acid chloride of carboxylic acid corresponding to benzoic acid derivative, according to the following reaction scheme in accordance with the method described in, for example, J. Chem. Soc., Vol. 1934, p. 1406, etc.

  (III)

wherein Ar has the same meaning as defined above.

SYNTHETIC METHOD 2

Synthesis of the compound (I-b) can be carried out in the same manner as in Synthetic method 1 except for using a compound (IV) in place of the starting compound (II).

The compound (IV) to be used in the present invention can be synthesized by isomerizing the compound (II) in sulfuric acid or by reacting perfluoro-(2-methyl-2-pentene) and N-methylthiourea in accordance with the method as described in Japanese Provisional Patent Publication No. 57371/1983, etc.

SYNTHETIC METHOD 3

Synthesis of the compound (I-c) of the present invention can be carried out by reacting the compound (I-b) with a thiocarbonylation reagent such as phosphorus pentasulfate, Lawesson's reagent and hydrogen sulfide as shown below.

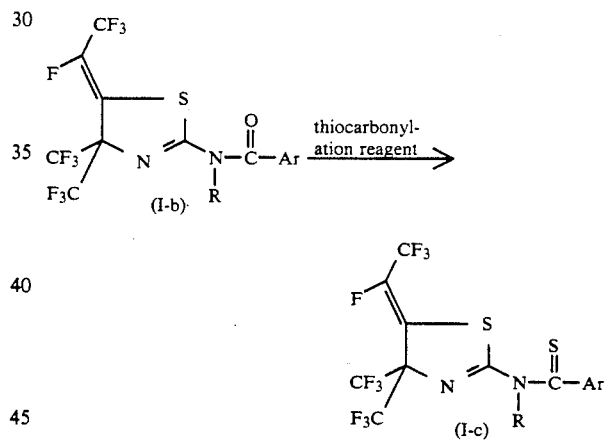

wherein Ar and R have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloromethane, dichloroethane, trichloroethylene and cyclohexane; ethers such as diethyl ether, tetrahydrofuran and dioxane; alcohols such as methanol, ethanol and ethylene glycol or hydrates thereof; dimethyl sulfoxide; carbon disulfide; and a mixture of the above solvents.

The solvent may be used such an amount that a concentration of the compound (I-b) is in the range of 5 to 80% by weight, but preferably such an amount that the concentration of the compound (I-b) is in the range of 10 to 70% by weight.

The reaction temperature is not particularly limited, but it is generally carried out in the temperature range of from room temperature to a boiling point or lower of a solvent used.

The reaction time varies depending on the above concentration of the starting material and the temperature, but may be generally 0.3 to 24 hours.

SYNTHETIC METHOD 4

Synthesis of the compound (I-d) or (I'') can be carried out by reacting the starting compound (II) and the starting compound (V) in the presence or absence of a solvent as shown below. Also, in order to accelerate the reaction, a base is frequently used as a catalyst.

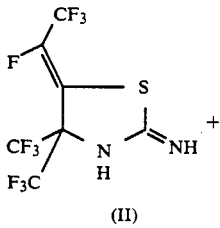

(II)

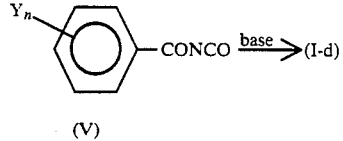

(V)

wherein Y and n have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloromethane, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; organic bases such as triethylamine, pyridine and N,N-dimethylaniline; 1,3-dimethyl-2-imidazolidinone; dimethyl sulfoxide; and a mixture of the above solvents.

The solvent may be used such an amount that a concentration of the compound (II) is in the range of 5 to 80% by weight, but preferably such an amount that the concentration of the compound (II) is in the range of 10 to 70% by weight.

The base to be used as a catalyst is not particularly limited, but there may be mentioned, for example, organic bases such as triethylamine, pyridine, 4-(N,N-dimethylamino)pyridine, N,N-dimethylaniline and DBU (1,8-diazabicyclo[5.4.0]undec-7-ene).

The base may be used in an amount of 0.001 to 5-fold mole per mole of the compound (II).

The reaction temperature is not particularly limited, but it is generally carried out in the temperature range of from room temperature to a boiling point or lower of a solvent used.

The reaction time varies depending on the above concentration of the starting material and the temperature, but may be generally 0.3 to 24 hours.

The starting compound (V) may be used in an amount of 0.5 to 2-fold mole based on the mole of the starting compound (II), but preferably 0.8 to 1.5-fold mole.

The compound (II) to be used in the present invention can be easily produced by using perfluoro-(2-methyl-2-pentene), etc. and thiourea according to the method described in, for example, Japanese Provisional Patent Publication No. 57371/1983, etc.

The compound (V) to be used in the present invention can be produced according to the following reaction scheme in accordance with the method described in, for example, Org. Synth., Vol. 46, p. 16, (1963), etc.

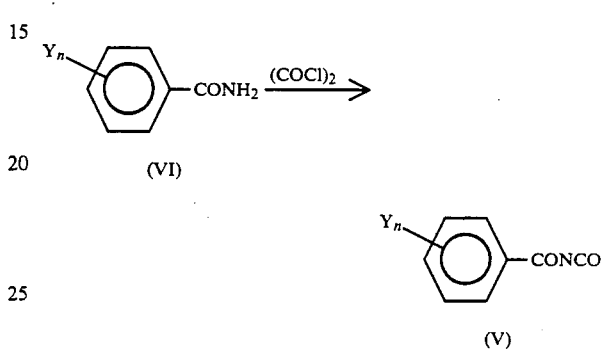

wherein Y and n have the same meanings as defined above.

As the compound (V), for example, each compound (referred to as Compound (V)$_{48}$ to (V)$_{75}$) comprising respective kinds of substituents corresponding to Compounds No. 48 to 75 shown in Table 1 below may be mentioned (for example, compound (V) corresponding to Compound No. 48 is referred to as Compound (V)$_{48}$. Compound (V)$_{48}$ is a compound wherein Y$_n$ in the formula (V) is 2,6-Cl$_2$.).

The desired compound (I) as mentioned above can be optionally purified, after completion of the reaction, by the conventional post-treatment such as extraction, condensation and filtration, and if necessary, by the known means such as recrystallization and various kinds of chromatographies.

As the compound (I), for example, each compound (referred to as Compound (I)$_1$ to (I)$_{75}$) comprising respective kinds of substituents corresponding to Compounds No. 1 to 75 shown in Table 1 below may be mentioned (for example, compound (I) corresponding to Compound No. 1 is referred to as Compound (I)$_1$. Compound (I)$_1$ is a compound wherein R in the formula (V) is H, X is O and Ar is 2,6-F$_2$ phenyl group.).

As the noxious organisms on which controlling effect by the desired compound (I) of the present invention can be observed, there may be mentioned agricultural and horticultural noxious insects (e.g. Hemiptera (e.g. planthoppers, leafhoppers, aphids and whiteflies), Lepidoptera (e.g. cabbage armyworms, diamondback moth, leafroller moths, pyralid moths and common cabbage worm), Coleoptera (e.g. tenebrionid beetles, leaf beetles, weevils and scarabs) and Acarina (e.g. citrus red mite and two-spotted spider mite of Tetranychidae family, and pink citrus rust mite of Eriophyidae family)), hygienically noxious insects (e.g. flies, mosquitos and cockroaches), noxious insects of stored grains, and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

The chemical for controlling noxious organisms of the present invention has remarkable insecticidal, acaricidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dust, an emulsion, a fine granule, a granule, a wettable powder, an aqueous or oily suspension and an aerosol) according to a conventional method.

As the carrier, there may be mentioned, for example, a solid carrier such as talc, bentonite, clay, kaolin, diatomaceous earth, white carbon, vermiculite, slaked lime, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethylsulfoxide) and water; and a gas carrier such as air, nitrogen, carbon dioxide and freon (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignin sulfonate and polyoxyethylene glycol ether. Further, for improving properties of its preparation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These medical preparations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these examples.

EXAMPLE 1

Synthesis of Compound (1)

The starting compound (II) was synthesized as described below.

(1) Synthesis of 2-(2,6-difluorobenzoylamino)-4,4-bis(trifluoromethyl)-5-(tetrafluoroethylidene)-2-thiazoline (Compound 1)

(a) According to Synthetic method 1, Compound 1 was synthesized as follows.

In toluene (10 ml) were dissolved 2-imino-4,4-bis(trifluoromethyl)-5-(tetrafluoroethylidene)-1,3-thiazolidine (0.8 g), triethylamine (1 ml) and a catalytic amount of 4-(N,N-dimethylamino)pyridine, and 2,6-difluorobenzoyl chloride (0.5 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate = 10:1) to obtain 0.5 g of the title compound (I) as a colorless crystal.

(b) According to Synthetic method 2, Compound 1 was synthesized as follows.

In toluene (10 ml) were dissolved 2-amino-4,4-bis(trifluoromethyl)-5-(tetrafluoroethylidene)-2-thiazoline (0.4 g), triethylamine (1 ml) and a catalytic amount of 4-(N,N-dimethylamino)pyridine, and 2,6-difluorobenzoyl chloride (0.2 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate = 10:1) to obtain 0.3 g of the title compound (I) as a colorless crystal.

(2) Synthesis of 2-benzoylamino-4,4-bis(trifluoromethyl)-5-(tetrafluoroethylidene)-2-thiazoline (Compound 2)

According to Synthetic method 1, Compound 2 was synthesized as follows.

In toluene (10 ml) were dissolved 2-imino-4,4-bis(trifluoromethyl)-5-(tetrafluoroethylidene)-1,3-thiazolidine (0.7 g) and triethylamine (1 ml), and benzoyl chloride (0.3 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate = 10:1) to obtain 0.4 g of the title compound (I) as a colorless crystal.

(3) Synthesis of 2-(4-chlorobenzoylamino)-4,4-bis(trifluoromethyl)-5-(tetrafluoroethylidene)-2-thiazoline (Compound 3)

According to Synthetic method 1, Compound 3 was synthesized as follows.

In toluene (15 ml) were dissolved 2-imino-4,4-bis(trifluoromethyl)-5-(tetrafluoroethylidene)-1,3-thiazolidine (4.0 g) and triethylamine (1.5 ml), and 4-chlorobenzoyl chloride (2.5 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.93 g of the title compound (I) as a colorless crystal.

(4) Synthesis of 2-(2-chlorobenzoylamino)-4,4-bis(trifluoromethyl)-5-(tetrafluoroethylidene)-2-thiazoline (Compound 4)

According to Synthetic method 1, Compound 4 was synthesized as follows.

In toluene (40 ml) were dissolved 2-imino-4,4-bis(trifluoromethyl)-5-(tetrafluoroethylidene)-1,3-thiazolidine (2.0 g) and triethylamine (1.0 ml), and a solution of 2-chlorobenzoyl chloride (1.3 g) dissolved in toluene (10 ml) was gradually added thereto under cooling and the mixture was stirred at room temperature for 4 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.21 g of the title compound (I) as a colorless crystal.

(5) Synthesis of 2-(3-chlorobenzoylamino)-4,4-bis(trifluoromethyl)-5-(tetrafluoroethylidene)-2-thiazoline (Compound 5)

According to Synthetic method 1, Compound 5 was synthesized as follows.

In toluene (20 ml) were dissolved 2-imino-4,4-bis(trifluoromethyl)-5-(tetrafluoroethylidene)-1,3-thiazolidine (2.0 g) and triethylamine (2.0 ml), and 3-chlorobenzoyl chloride (2.0 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting pale yellowish crystal was washed with n-hexane to obtain 0.51 g of the title compound (I) as a colorless crystal.

(6) Synthesis of 2-(2-methoxybenzoylamino)-4,4-bis(trifluoromethyl)-5-(tetrafluoroethylidene)-2-thiazoline (Compound 6)

According to Synthetic method 1, Compound 6 was synthesized as follows.

In toluene (10 ml) were dissolved 2-imino-4,4-bis(trifluoromethyl)-5-(tetrafluoroethylidene)-1,3-thiazolidine (1.0 g) and triethylamine (0.4 ml), and 2-methoxybenzoyl chloride (0.7 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.2 g of the title compound (I) as a colorless crystal.

(7) Synthesis of 2-(4-methylbenzoylamino)-4,4-bis(trifluoromethyl)-5-(tetrafluoroethylidene)-2-thiazoline (Compound 7)

According to Synthetic method 1, Compound 7 was synthesized as follows.

In toluene (10 ml) were dissolved 2-imino-4,4-bis(trifluoromethyl)-5-(tetrafluoroethylidene)-1,3-thiazolidine (0.5 g) and triethylamine (1.0 ml), and 4-methylbenzoyl chloride (0.3 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.3 g of the title compound (I) as a colorless crystal.

(8) Synthesis of 2-(2,6-dichlorobenzoylamino-4,4-bis(trifluoromethyl)-5-(tetrafluoroethylidene)-2-thiazoline (Compound 8)

According to Synthetic method 1, Compound 8 was synthesized as follows.

In toluene (10 ml) were dissolved 2-imino-4,4-bis(trifluoromethyl)-5-(tetrafluoroethylidene)-1,3-thiazolidine (0.5 g) and triethylamine (1.0 ml), and 2,6-dichlorobenzoyl chloride (0.4 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.4 g of the title compound (I) as a colorless crystal.

(9) Synthesis of 2-(3,5-dichlorobenzoylamino)-4,4-bis(trifluoromethyl)-5-(tetrafluoroethylidene)-2-thiazoline (Compound 9)

According to Synthetic method 1, Compound 9 was synthesized as follows.

In toluene (10 ml) were dissolved 2-imino-4,4-bis(trifluoromethyl)-5-(tetrafluoroethylidene)-1,3-thiazolidine (1.0 g) and triethylamine (1.0 ml), and 3,5-dichlorobenzoyl chloride (1.5 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.4 g of the title compound (I) as a colorless crystal.

(10) Synthesis of 2-(3,4-dichlorobenzoylamino)-4,4-bis(trifluoromethyl)-5-(tetrafluoroethylidene)-2-thiazoline (Compound 10)

According to Synthetic method 1, Compound 10 was synthesized as follows.

In toluene (10 ml) were dissolved 2-imino-4,4-bis(trifluoromethyl)-5-(tetrafluoroethylidene)-1,3-thiazolidine (1.1 g) and triethylamine (1.0 ml), and 3,4-dichlorobenzoyl chloride (1.0 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.9 g of the title compound (I) as a colorless crystal.

(11) Synthesis of 2-(4-nitrobenzoylamino)-4,4-bis(trifluoromethyl)-5-(tetrafluoroethylidene)-2-thiazoline (Compound 11)

According to Synthetic method 1, Compound 11 was synthesized as follows.

In toluene (10 ml) were dissolved 2-imino-4,4-bis(trifluoromethyl)-5-(tetrafluoroethylidene)-1,3-thiazolidine (0.5 g) and triethylamine (1.0 ml), and 4-nitrobenzoyl chloride (0.5 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.2 g of the title compound (I) as a colorless crystal.

(12) Synthesis of 2-(4-t-butylbenzoylamino)-4,4-bis(trifluoromethyl)-5-(tetrafluoroethylidene)-2-thiazoline (Compound 12)

According to Synthetic method 1, Compound 12 was synthesized as follows.

In toluene (10 ml) were dissolved 2-imino-4,4-bis(trifluoromethyl)-5-(tetrafluoroethylidene)-1,3-thiazolidine (1.0 g) and triethylamine (0 4 ml), and 4-t-butylbenzoyl chloride (0.9 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:ethyl acetate=10:1) to obtain 0.21 g of the title compound (I) as a colorless crystal.

(13) Synthesis of 2-(3-methoxybenzoylamino)-4,4-bis(trifluoromethyl)-5-(tetrafluoroethylidene)-2-thiazoline (Compound 13)

According to Synthetic method 1, Compound 13 was synthesized as follows.

In toluene (10 ml) were dissolved 2-imino-4,4-bis(trifluoromethyl)-5-(tetrafluoroethylidene)-1,3-thiazolidine (1.0 g) and triethylamine (0.4 ml), and 3-methoxybenzoyl chloride (0.7 g) was gradually added thereto and the mixture was stirred at room temperature for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.21 g of the title compound (I) as a colorless crystal.

(14) Synthesis of 2-(3-trifluoromethylbenzoylamino)-4,4-bis(trifluoromethyl)-5-(tetrafluoroethylidene)-2-thiazoline (Compound 14)

According to Synthetic method 1, Compound 14 was synthesized as follows.

In toluene (40 ml) were dissolved 2-imino-4,4-bis(trifluoromethyl)-5-(tetrafluoroethylidene)-1,3-thiazolidine (2.0 g) and triethylamine (1.0 ml), and a solution of 3-trifluoromethylbenzoyl chloride (1.5 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.44 g of the title compound (I) as a colorless crystal.

(15) Synthesis of 2-(3-nitrobenzoylamino)-4,4-bis(trifluoromethyl)-5-(tetrafluoroethylidene)-2-thiazoline (Compound 15)

According to Synthetic method 1, Compound 15 was synthesized as follows.

In toluene (40 ml) were dissolved 2-imino-4,4-bis(trifluoromethyl)-5-(tetrafluoroethylidene)-1,3-thiazolidine (2.0 g) and triethylamine (1.0 ml), and a solution of 3-nitrobenzoyl chloride (1.3 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.32 g of the title compound (I) as a colorless crystal.

(16) Synthesis of 2-(4-trifluoromethylbenzoylamino)-4,4-bis(trifluoromethyl)-5-(tetrafluoroethylidene)-2-thiazoline (Compound 16)

According to Synthetic method 1, Compound 16 was synthesized as follows.

In toluene (40 ml) were dissolved 2-imino-4,4-bis(trifluoromethyl)-5-(tetrafluoroethylidene)-1,3-thiazolidine (2.0 g) and triethylamine (1.0 ml), and a solution of 4-trifluoromethylbenzoyl chloride (1.5 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.6 g of the title compound (I) as a colorless crystal.

(17) Synthesis of 2-(3-fluorobenzoylamino)-4,4-bis(trifluoromethyl)-5-(tetrafluoroethylidene)-2-thiazoline (Compound 17)

According to Synthetic method 1, Compound 17 was synthesized as follows.

In dichloromethane (10 ml) were dissolved 2-imino-4,4-bis(trifluoromethyl)-5-(tetrafluoroethylidene)-1,3-thiazolidine (1.0 g) and dicyclohexylcarbodiimide (2.4 g), and a solution of 3-fluorobenzoic acid (1.6 g) dissolved in dichloromethane (10 ml) was gradually added thereto and the mixture was stirred at room temperature for 3 hours.

After the reaction, the reaction mixture was filtered and the resulting mother liquor was extracted with ethyl acetate. The extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.5 g of the title compound (I) as a colorless crystal.

(18) Synthesis of 2-(4-cyanobenzoylamino)-4,4-bis(trifluoromethyl)-5-(tetrafluoroethylidene)-2-thiazoline (Compound 20)

According to Synthetic method 1, Compound 20 was synthesized as follows.

In toluene (40 ml) were dissolved 2-imino-4,4-bis(trifluoromethyl)-5-(tetrafluoroethylidene)-1,3-thiazolidine (2.0 g) and triethylamine (1.0 ml), and a solution of 4-cyanobenzoyl chloride (1.2 g) dissolved in a mixed solution of toluene (10 ml) and dichloromethane (2 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 1.15 g of the title compound (I) as a colorless crystal.

(19) Synthesis of 2-(4-fluorobenzoylamino)-4,4-bis(trifluoromethyl)-5-(tetrafluoroethylidene)-2-thiazoline (Compound 21)

According to Synthetic method 1, Compound 21 was synthesized as follows.

In toluene (40 ml) were dissolved 2-imino-4,4-bis(trifluoromethyl)-5-(tetrafluoroethylidene)-1,3-thiazolidine (2.0 g) and triethylamine (0.6 ml), and a solution of 4-fluorobenzoyl chloride (0.8 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 1.53 g of the title compound (I) as a colorless crystal.

(20) Synthesis of 2-(3-bromobenzoylamino)-4,4-bis(trifluoromethyl)-5-(tetrafluoroethylidene)-2-thiazoline (Compound 23)

According to Synthetic method 1, Compound 23 was synthesized as follows.

In toluene (80 ml) were dissolved 2-imino-4,4-bis(trifluoromethyl)-5-(tetrafluoroethylidene)-1,3-thiazolidine (5.0 g) and triethylamine (1.5 ml), and a solution of 3-bromobenzoyl chloride (2.9 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.96 g of the title compound (I) as a colorless crystal.

(21) synthesis of 2-(3-trifluoromethoxybenzoylamino)-4,4-bis(trifluoromethyl)-5-(tetrafluoroethylidene)-2-thiazoline (Compound 36)

According to Synthetic method 1, Compound 36 was synthesized as follows.

In toluene (10 ml) were dissolved 2-imino-4,4-bis(trifluoromethyl)-5-(tetrafluoroethylidene)-1,3-thiazolidine (1.0 g) and triethylamine (0.6 ml), and a solution of 3-trifluoromethoxybenzoyl chloride (0.5 g) dissolved in toluene (10 ml) was gradually added thereto under cooling and the mixture was stirred at 103° C. for 3 hours.

After the reaction, the reaction mixture was extracted with ethyl acetate, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.7 g of the title compound (I) as a colorless crystal.

(22) Synthesis of 2-[(4-trifluoromethyl)thiobenzoylamino]-4,4-bis(trifluoromethyl)-5-(tetrafluoroethylidene)-2-thiazoline (Compound 37)

According to Synthetic method 3, Compound 37 was synthesized as follows.

In xylene (10 ml) was dissolved 2-(4-trifluoromethylbenzoylamino)-4,4-bis(trifluoromethyl)-5-(tetrafluoroethylidene)-2-thiazoline (1.0 g), and phosphorus pentasulfide (0.2 g) was added thereto and the mixture was refluxed for 2 hours.

After the reaction, the reaction mixture was extracted with toluene, and the extract was washed with water and dried over anhydrous sodium sulfate, and then the solvent was removed under reduced pressure.

The resulting oily product was purified by column chromatography (Wako gel C-200 (trade name, produced by Wako Junyaku K.K.), eluted by toluene:n-hexane=3:2) to obtain 0.5 g of the title compound (I) as a colorless crystal.

(23) Synthesis of 1-[4,4-bis(trifluoromethyl)-5-(tetrafluoroethylidene)-2-thiazolin-2-yl]-3-(2,6-difluorobenzoyl)urea (Compound 49)

According to Synthetic method 4, Compound 49 was synthesized as follows.

In toluene (10 ml) was dissolved 2-imino-4,4-bis(trifluoromethyl)-5-(tetrafluoroethylidene)-1,3-thiazolidine (1.0 g), and 2,6-difluorobenzoylisocyanate (0.4 g) which is a starting compound was added thereto and the mixture was stirred at room temperature for 3 hours.

After the reaction, the solvent was removed under reduced pressure. The resulting pale yellowish crystal was recrystallized from toluene-n-hexane to obtain 1.1 g of the title compound as a colorless crystal.

(24) Synthesis of 1-[4,4-bis(trifluoromethyl)-5-(tetrafluoroethylidene)-2-thiazolin-2-yl]-3-(2-chlorobenzoyl)urea (Compound 55)

According to Synthetic method 4, Compound 55 was synthesized as follows.

In toluene (10 ml) was dissolved 2-imino-4,4-bis(trifluoromethyl)-5-(tetrafluoroethylidene)-1,3-thiazolidine (1.0 g), and 2-chlorobenzoylisocyanate (0.4 g) which is a starting compound was added thereto and the mixture was stirred at room temperature for 3 hours.

After the reaction, the solvent was removed under reduced pressure. The resulting pale yellowish crystal was recrystallized from toluene-n-hexane to obtain 0.7 g of the title compound as a colorless crystal.

(25) Synthesis of 1-[4,4-bis(trifluoromethyl)-5-(tetrafluoroethylidene)-2-thiazolin-2-yl]-3-(2-methylbenzoyl)urea (Compound 57)

According to Synthetic method 4, Compound 57 was synthesized as follows.

In toluene (10 ml) was dissolved 2-imino-4,4-bis(trifluoromethyl)-5-(tetrafluoroethylidene)-1,3-thiazolidine (1.0 g), and 2-methylbenzoylisocyanate (0.3 g) which is a starting compound was added thereto and the mixture was stirred at room temperature for 3 hours.

After the reaction, the solvent was removed under reduced pressure. The resulting pale yellowish crystal was recrystallized from toluene-n-hexane to obtain 0.6 g of the title compound as a colorless crystal.

(26) Synthesis of 1-[4,4-bis(trifluoromethyl)-5-(tetrafluoroethylidene)-2-thiazolin-2-yl]-3-(2-methoxybenzoyl)urea (Compound 58)

According to Synthetic method 4, Compound 58 was synthesized as follows.

In toluene (10 ml) was dissolved 2-imino-4,4-bis(trifluoromethyl)-5-(tetrafluoroethylidene)-1,3-thiazolidine (1.0 g), and 2-methoxybenzoylisocyanate (0.4 g) which is a starting compound was added thereto and the mixture was stirred at room temperature for 3 hours.

After the reaction, the solvent was removed under reduced pressure. The resulting pale yellowish crystal was recrystallized from toluene-n-hexane to obtain 0.7 g of the title compound as a colorless crystal.

(27) Synthesis of 1-[4,4-bis(trifluoromethyl)-5-(tetrafluoroethylidene)-2-thiazolin-2-yl]-3-(2-nitrobenzoyl)urea (Compound 60)

According to Synthetic method 4, Compound 60 was synthesized as follows.

In toluene (10 ml) was dissolved 2-imino-4,4-bis(trifluoromethyl)-5-(tetrafluoroethylidene)-1,3-thiazolidine (1.0 g), and 2-nitrobenzoylisocyanate (0.4 g) which is a starting compound was added thereto and the mixture was stirred at room temperature for 3 hours.

After the reaction, the solvent was removed under reduced pressure. The resulting pale yellowish crystal was recrystallized from toluene-n-hexane to obtain 0.5 g of the title compound as a colorless crystal.

The compounds of the present invention are enumerated in the following Table 1, respectively.

TABLE 1

| Compound No. | R | X | Ar | Physical property |
|---|---|---|---|---|
| 1 | H | O | 2,6-difluorophenyl | m. p. 122~124° C. |
| 2 | " | " | phenyl | m. p. 78–80° C. |
| 3 | " | " | 4-chlorophenyl | m. p. 118~121° C. |
| 4 | " | " | 2-chlorophenyl | m. p. 141~142° C. |
| 5 | " | " | 3-chlorophenyl | m. p. 193~194° C. |
| 6 | " | " | 2-methoxyphenyl | m. p. 137~138° C. |
| 7 | " | " | 4-methylphenyl | m. p. 127~128° C. |
| 8 | " | " | 2,4-dichlorophenyl | m. p. 142–144° C. |

TABLE 1-continued

| # | | | Ar | m.p. |
|---|---|---|---|---|
| 9 | " | " | 3,4-dichlorophenyl | m.p. 142~143° C. |
| 10 | " | " | 2,3-dichlorophenyl | m.p. 198~202° C. |
| 11 | H | O | 4-nitrophenyl | m.p. 233~234° C. |
| 12 | " | " | 4-tert-butylphenyl | m.p. 149~150° C. |
| 13 | " | " | 4-methoxyphenyl | m.p. 155~157° C. |
| 14 | " | " | 3-CF$_3$-phenyl | m.p. 199~200° C. |
| 15 | " | " | 3-nitrophenyl | m.p. 199~200° C. |
| 16 | " | " | 4-CF$_3$-phenyl | m.p. 167~168° C. |
| 17 | " | " | 3-fluorophenyl | m.p. 166~167° C. |
| 18 | " | " | 3,4-dichlorophenyl | m.p. 127~128° C. |
| 19 | " | " | 2,3,4,5-tetrafluorophenyl | m.p. 138~140° C. |
| 20 | " | " | 4-cyanophenyl | m.p. 182~183° C. |
| 21 | H | O | 4-fluorophenyl | m.p. 170~171° C. |
| 22 | " | " | 4-phenoxyphenyl | m.p. 157~158° C. |
| 23 | " | " | 4-bromophenyl | m.p. 134~135° C. |
| 24 | " | " | 3-benzyloxyphenyl | m.p. 152~153° C. |
| 25 | " | " | 3-phenoxyphenyl | m.p. 150~151° C. |
| 26 | " | " | 4-N(CH$_3$)$_2$-phenyl | m.p. 191~192° C. |
| 27 | " | " | 4-hydroxyphenyl | m.p. 180~181° C. |
| 28 | " | " | 3-NO$_2$-4-Cl-phenyl | m.p. 230~231° C. |
| 29 | CH$_3$ | " | 4-bromophenyl | m.p. 140~143° C. |
| 30 | H | " | 3,4-dinitrophenyl | m.p. 185~187° C. |
| 31 | H | O | 3,4-dinitrophenyl | m.p. 217~218° C. |
| 32 | " | " | 2-carboxyphenyl | m.p. 189~190° C. |
| 33 | " | " | 4-OCF$_3$-phenyl | m.p. 132~133° C. |
| 34 | " | " | 3-F-4-CF$_3$-phenyl | m.p. 185~187° C. |

TABLE 1-continued

| # | | | Ar | Physical property |
|---|---|---|---|---|
| 35 | " | " | 4-Cl-3,5-(NO$_2$)$_2$-C$_6$H$_2$ (2-Cl-4,6-dinitrophenyl) | m.p. 134~136° C. |
| 36 | " | " | 4-OCF$_3$-C$_6$H$_4$ | m.p. 150~151° C. |
| 37 | " | S | 4-CF$_3$-C$_6$H$_4$ | m.p. 105~106° C. |
| 38 | CH$_3$ | O | 3,4-F$_2$-C$_6$H$_3$ | m.p. 69~71° C. |
| 39 | H | " | 4-SO$_2$CH$_3$-C$_6$H$_4$ | m.p. 223~225° C. |
| 40 | " | " | 3,4-F$_2$-C$_6$H$_3$ | m.p. 153~154° C. |
| 41 | H | O | 4-(OCF$_2$CHFCl)-C$_6$H$_4$ | m.p. 115~117° C. |
| 42 | " | " | 4-SCH$_3$-C$_6$H$_4$ | m.p. 135~137° C. |
| 43 | " | " | 2-naphthyl | m.p. 118~120° C. |
| 44 | " | " | 1-naphthyl | m.p. 129~130° C. |
| 45 | " | " | 4-(4-F-C$_6$H$_4$-O)-C$_6$H$_4$ | m.p. 152~153° C. |
| 46 | " | " | 2-Cl-4-NO$_2$-C$_6$H$_3$ | m.p. 113~115° C. |
| 47 | " | " | 3,4-methylenedioxyphenyl | m.p. 139~142° C. |

TABLE 1-continued $$\text{structure with } CF_3, F_3C, F_3C, S, N, NHCONHCO-C_6H_4-Y_n$$

Ar = -C$_6$H$_4$-Y$_n$

| Compound No. | Ar | Physical property |
|---|---|---|
| 48 | 2,3-Cl$_2$-C$_6$H$_3$ | m.p. 190~192° C. |
| 49 | 2,4-F$_2$-C$_6$H$_3$ | m.p. 188~190° C. |
| 50 | C$_6$H$_5$ | m.p. 145~147° C. |
| 51 | 2-Cl-C$_6$H$_4$ | m.p. 164~167° C. |
| 52 | 4-CF$_3$-C$_6$H$_4$ | m.p. 153~154° C. |
| 53 | 4-NO$_2$-C$_6$H$_4$ | m.p. 207~209° C. |
| 54 | 4-Br-C$_6$H$_4$ | m.p. 184~186° C. |
| 55 | 2-Cl-C$_6$H$_4$ | m.p. 152~153° C. |
| 56 | 2-F-C$_6$H$_4$ | m.p. 161~162° C. |
| 57 | 2-CH$_3$-C$_6$H$_4$ | m.p. 115~117° C. |
| 58 | 2-OCH$_3$-C$_6$H$_4$ | m.p. 177~178° C. |

TABLE 1-continued

| # | Substituent | m.p. |
|---|---|---|
| 59 | 4-CN-C₆H₄- | m. p. 163~165° C. |
| 60 | 2-O₂N-C₆H₄- | m. p. 196~197° C. |
| 61 | 3-OCF₃-C₆H₄- | m. p. 127~129° C. |
| 62 | 2,5-Cl₂-C₆H₃- | m. p. 189~190° C. |
| 63 | 2-Cl-5-NO₂-C₆H₃- | m. p. 205~206° C. |
| 64 | 2-H₃COC-C₆H₄- | m. p. 240° C. or more |
| 65 | 2,5-F₂-C₆H₃- | m. p. 151~152° C. |
| 66 | 2-F₃C-C₆H₄- | m. p. 159~160° C. |
| 67 | 2-naphthyl | m. p. 200~202° C. |
| 68 | 1-naphthyl | m. p. 174~175° C. |
| 69 | 2,3,5,6-F₄-C₆H- | m. p. 131~132° C. |
| 70 | 2,3,5-Cl₃-C₆H₂- | m. p. 207~209° C. |
| 71 | 3-Br-C₆H₄- | m. p. 172~173° C. |
| 72 | 2,3-Cl₂-C₆H₃- | m. p. 149~152° C. |
| 73 | 2-F-5-Cl-C₆H₃- | m. p. 192~194° C. |
| 74 | 2-HF₂C-C₆H₄- | |
| 75 | 2-FH₂C-C₆H₄- | |

In the above exemplary compounds, preferred are as shown below:

2-(2,6-difluorobenzoylamino)-4,4-bis(trifluoromethyl)-5-(tetrafluoroethylidene)-2-thiazoline,
2-(4-chlorobenzoylamino)-4,4-bis(trifluoromethyl)-5-(tetrafluoroethylidene)-2-thiazoline,
2-(3-chlorobenzoylamino)-4,4-bis(trifluoromethyl)-5-(tetrafluoroethylidene)-2-thiazoline,
2-(3,5-dichlorobenzoylamino)-4,4-bis(trifluoromethyl)-5-(tetrafluoroethylidene)-2-thiazoline,
2-(3,4-dichlorobenzoylamino)-4,4-bis(trifluoromethyl)-5-(tetrafluoroethylidene)-2-thiazoline,
2-(3-trifluoromethylbenzoylamino)-4,4-bis(trifluoromethyl)-5-(tetrafluoroethylidene)-2-thiazoline,
2-(3-nitrobenzoylamino)-4,4-bis(trifluoromethyl)-5-(tetrafluoroethylidene)-2-thiazoline,
2-(4-trifluoromethylbenzoylamino)-4,4-bis(trifluoromethyl)-5-(tetrafluoroethylidene)-2-thiazoline,
2-(3-fluorobenzoylamino)-4,4-bis(trifluoromethyl)-5-(tetrafluoroethylidene)-2-thiazoline,
2-(2,4-dichlorobenzoylamino)-4,4-bis(trifluoromethyl)-5-(tetrafluoroethylidene)-2-thiazoline,
2-(4-cyanobenzoylamino)-4,4-bis(trifluoromethyl)-5-(tetrafluoroethylidene)-2-thiazoline,
2-(4-fluorobenzoylamino)-4,4-bis(trifluoromethyl)-5-(tetrafluoroethylidene)-2-thiazoline,
2-(3-bromobenzoylamino)-4,4-bis(trifluoromethyl)-5-(tetrafluoroethylidene)-2-thiazoline,
2-(4-trifluoromethoxybenzoylamino)-4,4-bis(trifluoromethyl)-5-(tetrafluoroethylidene)-2-thiazoline,
2-(4-fluoro-3-trifluoromethylbenzoylamino)-4,4-bis(trifluoromethyl)-5-(tetrafluoroethylidene)-2-thiazoline,
2-(3-trifluoromethoxybenzoylamino)-4,4-bis(trifluoromethyl)-5-(tetrafluoroethylidene)-2-thiazoline,
N-[4,4-bis(trifluoromethyl)-5-(tetrafluoroethylidene)-2-thiazolin-2-yl] 4-trifluoromethylbenzenethioamide,
2-(3,4-difluorobenzoylamino)-4,4-bis(trifluoromethyl)-5-(tetrafluoroethylidene)-2-thiazoline,
2-{4-(2-chloro-1,1,2-trifluoroethoxy)benzoylamino}-4,4-bis(trifluoromethyl)-5-(tetrafluoroethylidene)-2-thiazoline, 2-(2-chloro-4-nitrobenzoylamino)-4,4-bis(trifluoromethyl)-5-(tetrafluoroethylidene)-2-thiazoline,
1-[4,4-bis(trifluoromethyl)-5-(tetrafluoroethylidene)-2-thiazolin-2-yl]-3-(2,6-dichlorobenzoyl)urea,
1-[4,4-bis(trifluoromethyl)-5-(tetrafluoroethylidene)-2-thiazolin-2-yl]-3-(2,6-difluorobenzoyl)urea,
1-[4,4-bis(trifluoromethyl)-5-(tetrafluoroethylidene)-2-thiazolin-2-yl]-3-(2-chlorobenzoyl)urea,
1-[4,4-bis(trifluoromethyl)-5-(tetrafluoroethylidene)-2-thiazolin-2-yl]-3-(2-fluorobenzoyl)urea,
1-[4,4-bis(trifluoromethyl)-5-(tetrafluoroethylidene)-2-thiazolin-2-yl]-3-(2-methylbenzoyl)urea,
1-[4,4-bis(trifluoromethyl)-5-(tetrafluoroethylidene)-2-thiazolin-2-yl]-3-(2,4-dichlorobenzoyl)urea,
1-[4,4-bis(trifluoromethyl)-5-(tetrafluoroethylidene)2-thiazolin-2-yl]-3-(2-chloro-4-nitrobenzoyl)urea,
1-[4,4-bis(trifluoromethyl)-5-(tetrafluoroethylidene)-2-thiazolin-2-yl]-3-(2,4-difluorobenzoyl)urea,
1-[4,4-bis(trifluoromethyl)-5-(tetrafluoroethylidene)-2-thiazolin-2-yl]-3-(2-trifluoromethylbenzoyl)urea,
1-[4,4-bis(trifluoromethyl)-5-(tetrafluoroethylidene)-2-thiazolin-2-yl]-3-(2,4,6-trichlorobenzoyl)urea,
1-[4,4-bis(trifluoromethyl)-5-(tetrafluoroethylidene)-2-thiazolin-2-yl]-3-(2-bromobenzoyl)urea,
1-[4,4-bis(trifluoromethyl)-5-(tetrafluoroethylidene)-2-thiazolin-2-yl]-3-(2,3-dichlorobenzoyl)urea and
1-[4,4-bis(trifluoromethyl)-5-(tetrafluoroethylidene)-2-thiazolin-2-yl]-3-(2-chloro-6-fluorobenzoyl)urea.

Of these, particularly preferred are the following compounds:
2-(2,6-difluorobenzoylamino)-4,4-bis(trifluoromethyl)-5-(tetrafluoroethylidene)-2-thiazoline,
2-(4-chlorobenzoylamino)-4,4-bis(trifluoromethyl)-5-(tetrafluoroethylidene)-2-thiazoline,
2-(3-chlorobenzoylamino)-4,4-bis(trifluoromethyl)-5-(tetrafluoroethylidene)-2-thiazoline,
2-(3,5-dichlorobenzoylamino)-4,4-bis(trifluoromethyl)-5-(tetrafluoroethylidene)-2-thiazoline,
2-(3,4-dichlorobenzoylamino)-4,4-bis(trifluoromethyl)-5-(tetrafluoroethylidene)-2-thiazoline,
2-(3-trifluoromethylbenzoylamino)-4,4-bis(trifluoromethyl)-5-(tetrafluoroethylidene)-2-thiazoline,
2-(3-nitrobenzoylamino)-4,4-bis(trifluoromethyl)-5-(tetrafluoroethylidene)-2-thiazoline,
2-(4-trifluoromethylbenzoylamino)-4,4-bis(trifluoromethyl)-5-(tetrafluoroethylidene)-2-thiazoline,
2-(3-fluorobenzoylamino)-4,4-bis(trifluoromethyl)-5-(tetrafluoroethylidene)-2-thiazoline,
2-(2,4-dichlorobenzoylamino)-4,4-bis(trifluoromethyl)-5-(tetrafluoroethylidene)-2-thiazoline,
2-(4-cyanobenzoylamino)-4,4-bis(trifluoromethyl)-5-(tetrafluoroethylidene)-2-thiazoline,
2-(4-fluorobenzoylamino)-4,4-bis(trifluoromethyl)-5-(tetrafluoroethylidene)-2-thiazoline,
2-(3-bromobenzoylamino)-4,4-bis(trifluoromethyl)-5-(tetrafluoroethylidene)-2-thiazoline,
2-(4-trifluoromethoxybenzoylamino)-4,4-bis(trifluoromethyl)-5-(tetrafluoroethylidene)-2-thiazoline,
2-(4-fluoro-3-trifluoromethylbenzoylamino)-4,4-bis(trifluoromethyl)-5-(tetrafluoroethylidene)-2-thiazoline,
2-(3-trifluoromethoxybenzoylamino)-4,4-bis(trifluoromethyl)-5-(tetrafluoroethylidene)-2-thiazoline,
2-(3,4-difluorobenzoylamino)-4,4-bis(trifluoromethyl)-5-(tetrafluoroethylidene)-2-thiazoline,
2-(2-chloro-4-nitrobenzoylamino)-4,4-bis(trifluoromethyl)-5-(tetrafluoroethylidene)-2-thiazoline,
1-[4,4-bis(trifluoromethyl)-5-(tetrafluoroethylidene)-2-thiazolin-2-yl]-3-(2,6-difluorobenzoyl)urea,
1-[4,4-bis(trifluoromethyl)-5-(tetrafluoroethylidene)-2-thiazolin-2-yl]-3-(2-chlorobenzoyl)urea,
1-[4,4-bis(trifluoromethyl)-5-(tetrafluoroethylidene)-2-thiazolin-2-yl]-3-(2-fluorobenzoyl)urea,
1-[4,4-bis(trifluoromethyl)-5-(tetrafluoroethylidene)-2-thiazolin-2-yl]-3-(2-methylbenzoyl)urea and
1-[4,4-bis(trifluoromethyl)-5-(tetrafluoroethylidene)-2-thiazolin-2-yl]-3-(2-chloro-6-fluorobenzoyl)urea.

EXAMPLE 2

Preparation of formulation (1) Preparation of Granule

Five (5) parts by weight of Compound 1 was uniformly mixed with 35 parts by weight of bentonite, 57 parts by weight of talc, 1 part by weight of Neopelex powder (trade name, produced by Kao K.K.) and 2 parts by weight of lignin sodium sulfonate, and then the mixture was kneaded with addition of a small amount of water, followed by granulation and drying, to obtain a granule.

(2) Preparation of Wettable Powder

Ten (10) parts by weight of Compound 1 was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of Emulsion

Twenty (20) parts by weight of Compound 1 was uniformly mixed with 70 parts by weight of xylene by adding 10 parts by weight of Toxanone (trade name, produced by Sanyo Kasei Kogyo K.K.), and dissolved therein to obtain an emulsion.

(4) Preparation of Dust

Five (5) parts by weight of Compound 1 was uniformly mixed with 50 parts by weight of talc and 45 parts by weight of kaolin to obtain a dust.

EXAMPLE 3

(1) Activity Test Against Common Cutworm

The respective wettable powders of the compound (I) shown in Table 1 prepared in accordance with Example 2 were diluted to 500 ppm with water containing a surfactant (0.01%), and in these respective chemical solutions obtained, soybean leaves were dipped for 30 seconds, respectively. Then, one soybean leaf thus treated was placed in a plastic cup and air-dried.

Ten (10) common cutworms (2nd instar larvae) were freed in the respective cups and a lid was put on the cup. These cups were allowed to stand in a thermostat chamber at 25° C. Two (2) days later, the % mortality was determined by counting the numbers of living and dead insects in the respective cups.

The insecticidal effect of each chemical was evaluated by using 4 ranks depending on the % mortality (A: 100%, B: 99 to 80%, C: 79 to 60% and D: 59% or less).

As a comparative sample, the compound represented by the following formula (VII):

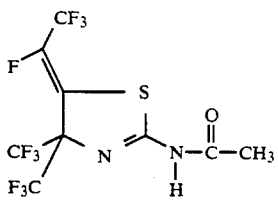 (VIII)

described in Japanese Provisional Patent Publication No. 57371/1983 was used to prepare a comparative preparation in the same manner as mentioned above. The same experiment was carried out for the comparative preparation. The results are shown in Table 2.

TABLE 2

| Compound | Effect |
|---|---|
| 1 | A |
| 3 | A |
| 5 | A |
| 9 | A |
| 10 | A |
| 14 | A |
| 15 | A |
| 16 | A |
| 17 | A |
| 18 | A |
| 20 | A |
| 21 | B |
| 23 | A |
| 33 | A |
| 34 | A |
| 36 | A |
| 37 | A |
| 40 | A |
| 41 | A |
| 45 | A |
| 46 | B |
| 49 | B |
| 55 | A |
| 56 | A |
| 57 | A |
| 58 | B |
| 61 | A |
| 62 | A |
| 63 | A |
| 65 | A |
| 66 | A |
| 70 | A |
| 71 | A |
| 72 | A |
| 73 | A |
| Comparative example | D |

(2) Activity Test Against Diamondback Moth

The respective wettable powders of the compound (I) shown in Table 1 prepared in accordance with Example 2 were diluted to 300 ppm with water containing a surfactant (0.01%), and in these respective chemical solutions obtained, cabbage leaves (5 cm×5 cm; were dipped for 30 seconds, respectively. Then, one cabbage leaf thus treated was placed in a plastic cup and air-dried.

Ten (10) diamondback moth (3rd instar larvae) were freed in the respective cups and a lid was put on the cup. These cups were allowed to stand in a thermostat chamber at 25° C. Two (2) days later, the % mortality was determined by counting the numbers of living and dead insects in the respective cups.

The insecticidal effect of each chemical was evaluated by using 4 ranks as described in the above (1) with the comparative sample prepared in the same manner as described in the above (1). The results are shown in Table 3.

TABLE 3

| Compound | Effect |
|---|---|
| 1 | A |
| 2 | A |
| 3 | A |
| 4 | A |
| 5 | A |
| 9 | A |
| 10 | A |
| 11 | A |
| 14 | A |
| 15 | A |
| 16 | A |
| 17 | A |
| 18 | A |
| 20 | A |
| 21 | A |
| 23 | A |
| 25 | A |
| 33 | A |
| 34 | A |
| 36 | A |
| 37 | A |
| 40 | A |
| 41 | A |
| 42 | A |
| 45 | A |
| 46 | A |
| 48 | A |
| 49 | A |
| 51 | A |
| 52 | A |
| 55 | A |
| 56 | A |
| 57 | A |
| 60 | A |
| 62 | A |
| 63 | A |
| 65 | A |
| 70 | A |
| 71 | A |
| 72 | A |
| 73 | A |
| Comparative example | D |

(3) Activity Test Against Confused Flour Beetle

The respective wettable powders of the compound (I) shown in Table 1 prepared in accordance with Example 2 were diluted to 500 ppm with water containing a surfactant (0.01%), and 1 ml of each chemical solution obtained was dropped thoroughly on a filter paper (7.8 cm in diameter, one piece of paper) in each of plastic cups and air-dried.

Ten (10) confused flour beetles (adult) were freed in the respective cups and a lid was put on the cup. These cups were allowed to stand in a thermostat chamber at 25° C. Five (5) days later, the % mortality was determined by counting the numbers of living and dead insects in the respective cups.

The insecticidal effect of each chemical was evaluated by using 4 ranks as described in the above (1) with the comparative sample prepared in the same manner as described in the above (1). The results are shown in Table 4.

TABLE 4

| Compound | Effect |
|---|---|
| 3 | A |
| 5 | A |
| 9 | A |
| 10 | A |
| 11 | A |
| 14 | A |

TABLE 4-continued

| Compound | Effect |
| --- | --- |
| 15 | A |
| 16 | A |
| 17 | B |
| 18 | A |
| 20 | B |
| 21 | A |
| 23 | A |
| 24 | B |
| 25 | A |
| 33 | A |
| 34 | A |
| 36 | A |
| 40 | A |
| 41 | A |
| 43 | B |
| 45 | A |
| 46 | A |
| 48 | A |
| 49 | A |
| 52 | A |
| 60 | A |
| 61 | A |
| 66 | A |
| 72 | A |
| Comparative example | D |

(4) Activity Test Against Female Adult Two-spotted Spider Mite

The respective wettable powders of the compound (I) shown in Table 2 prepared in accordance with Example 2 were diluted to 300 ppm with water containing a surfactant (0.01%), and in these respective chemical solutions obtained, kidney bean leaf strips (diameter: 20 mm) on which 10 female adult two-spotted spider mites were parasitic were dipped for 15 seconds, respectively.

Subsequently, these respective strips were allowed to stand in a thermostat chamber at 25° C. Three (3) days later, the % mortality was determined by counting the numbers of living and dead mites in the respective strips.

The acaricidal effect of each chemical was evaluated by using 4 ranks as described in the above (1) with the comparative sample prepared in the same manner as described in the above (1). The results are shown in Table 5.

TABLE 5

| Compound | Effect |
| --- | --- |
| 1 | A |
| 3 | A |
| 8 | B |
| 9 | A |
| 10 | A |
| 11 | A |
| 14 | A |
| 15 | A |
| 16 | A |
| 17 | A |
| 18 | A |
| 19 | A |
| 20 | A |
| 21 | A |
| 23 | A |
| 33 | A |
| 34 | A |
| 36 | A |
| 37 | A |
| 40 | A |
| 41 | B |
| 46 | A |
| Comparative example | D |

(5) Test of Controlling Effect on Brown Rust (Wheat) (Prevention Effect)

In plastic flowerpots 6 cm in diameter, 10 wheats (variety: Kobushi wheat) were grown per one flowerpot, and to the young plants at 1.5 leaf stage, the chemical solutions obtained by diluting the wettable powders of the compounds (I) shown in Table 1 prepared in accordance with Example 2 to 500 ppm with water containing a surfactant (0.05%) were sprayed in an amount of 20 ml per one flowerpot, respectively.

These wheats thus treated were grown in a glass greenhouse for 2 days, and then a spore suspension of brown rust ($7 \times 10^4$ spores/ml) was sprayed uniformly to the plants to be inoculated thereinto.

Subsequently, the wheats were grown in a glass greenhouse for one week, and the degree of lesion of brown rust appeared on the first leaves was examined.

The effect of each chemical was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

As a comparative sample, the compound represented by the formula (VII) was used to prepare a comparative preparation in the same manner as mentioned above. The same experiment was carried out for the comparative preparation. The results are shown in Table 6.

TABLE 6

| Compound | Effect |
| --- | --- |
| 1 | 4 |
| 4 | 5 |
| 9 | 4 |
| 14 | 4 |
| 15 | 5 |
| 16 | 5 |
| 18 | 5 |
| 19 | 5 |
| 21 | 5 |
| 23 | 4 |
| 34 | 5 |
| 36 | 5 |
| 37 | 5 |
| 40 | 5 |
| Comparative example | 0 |
| Non-treated district | 0 |

(6) Test of Controlling Effect on Powdery Mildew (Barley) (Prevention Effect)

In plastic flowerpots 6 cm in diameter, 10 barleys (variety: black barley) were grown per one flowerpot, and to the young plants at 1.5 leaf stage, the chemical solutions obtained by diluting the wettable powders of the compound (I) shown in Table 2 prepared in accordance with Example 2 to 500 ppm with water containing a surfactant (0.05%) were sprayed in an amount of 20 ml per one flowerpot, respectively.

These barleys were grown in a glass greenhouse for 2 days, and then conidiospores of powdery mildew collected from infected leaves was dusted thoroughly to the plant leaves to be inoculated thereinto. Subsequently, these barleys were grown in a glass greenhouse for a week, and the degree of lesion of powdery mildew (barley) appeared on the first leaves were examined.

The results evaluated by using the 6 ranks as described in the above (2) are shown in Table 7.

TABLE 7

| Compound | Effect |
|---|---|
| 3 | 4 |
| 5 | 5 |
| 9 | 5 |
| 10 | 5 |
| 14 | 4 |
| 18 | 5 |
| 21 | 5 |
| 23 | 4 |
| 40 | 5 |
| 41 | 4 |
| Comparative example | 0 |
| Non-treated district | 0 |

The novel thiazoline derivatives of the present invention can be used as agricultural chemicals useful as a chemical for controlling noxious organisms.

We claim:

1. A thiazoline compound represented by the following formula (I):

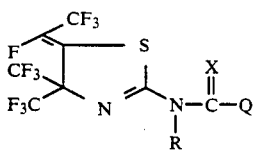
(I)

wherein
R represents a hydrogen atom or a lower alkyl group,
X represents an oxygen atom or a sulfur atom, and
Q represents Ar, wherein Ar represents
a phenyl group;
a phenyl group substituted by 1 to 5 substituents selected from the group consisting of a halogen atom, an alkoxy group having 1 to 6 carbon atoms, an alkyl group having 1 to 6 carbon atoms, a nitro group, a haloalkyl group having 1 to 6 carbon atoms, a cyano group, a phenyloxy group, a phenyloxy group substituted by a halogen atom, an aralkyloxy group, an aralkyloxy group substituted by a halogen atom, an alkylamino group having 1 to 6 carbon atoms, a hydroxyl group, a carboxyl group, a haloalkoxy group having 1 to 6 carbon atoms, an alkylsulfonyl group having 1 to 6 carbon atoms, an alkylthio group having 1 to 6 carbon atoms and a methylenedioxy group;
a naphthyl group; or
a naphthyl group substituted by a substituent selected from the group consisting of a halogen atom, an alkoxy group having 1 to 6 carbon atoms, an alkyl group having 1 to 6 carbon atoms, a nitro group, a haloalkyl group having 1 to 6 carbon atoms, a cyano group, a phenyloxy group, a phenyloxy group substituted by a halogen atom, an aralkyloxy group, an aralkyloxy group substituted by a halogen atom, an alkylamino group having 1 to 6 carbon atoms, a hydroxyl group, a carboxyl group, a haloalkoxy group having 1 to 6 carbon atoms, an alkylsulfonyl group having 1 to 6 carbon atoms, an alkylthio group having 1 to 6 carbon atoms and a methylenedioxy group, or
Q represents

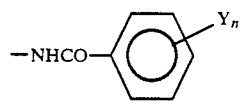

wherein Y represents a halogen atom, an alkyl group having 1 to 6 carbon atoms, an alkoxy group having 1 to 6 carbon atoms, an alkoxy group having 1 to 6 carbon atoms, a haloalkoxy group having 1 to 6 carbon atoms, a nitro group, an acetyl group or a cyano group and n represents an integer of 0 to 5 or n=2 and $Y_n$ represents an unsaturated 6-membered ring formed with carbon atoms to which the Ys are bonded and the 6-membered ring is fused to the benzene ring, provided that when Q is

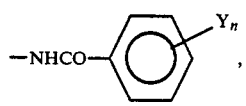

R is a hydrogen atom and X is an oxygen atom.

2. The compound according to claim 1, wherein the compound is represented by the formula (I'):

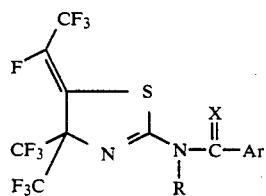
(I')

wherein
R represents a hydrogen atom or a lower alkyl group having 1 to 6 carbon atoms,
X represents an oxygen atom or a sulfur atom, and
Ar represents
a phenyl group;
a phenyl group substituted by 1 to 5 substituents selected from the group consisting of a halogen atom, an alkoxy group having 1 to 6 carbon atoms, an alkyl group having 1 to 6 carbon atoms, a nitro group, a haloalkyl group having 1 to 6 carbon atoms, a cyano group, a phenyloxy group, a phenyloxy group substituted by a halogen atom, an aralkyloxy group, an aralkyloxy group substituted by a halogen atom, an alkylamino group having 1 to 6 carbon atoms, a hydroxyl group, a carboxyl group, a haloalkoxy group having 1 to 6 carbon atoms, an alkylsulfonyl group having 1 to 6 carbon atoms, an alkylthio group having 1 to 6 carbon atoms and a methylenedioxy group;
a naphthyl group; or
a naphthyl group substituted by a substituent selected from the group consisting of a halogen atom, an alkoxy group having 1 to 6 carbon atoms, an alkyl group having 1 to 6 carbon atoms, a nitro group, a haloalkyl group having 1 to 6 carbon atoms, a cyano group, a phenyloxy group, a phenyloxy group substituted by a halogen atom, an aralkyloxy group, an aralkyloxy group substituted by a halogen atom, an alkylamino group having 1 to 6 carbon atoms, a hydroxyl group, a carboxyl group, a haloalkoxy group having 1 to 6 carbon atoms, an alkylsulfonyl group having 1 to 6 carbon atoms, an alkylthio group having 1 to 6 carbon atoms and a methylenedioxy group.

3. The compound according to claim 2, wherein the substituent for Ar is selected from the group consisting of a chlorine atom, a bromine atom, a fluorine atom, an iodine atom, an alkoxy group having 1 to 6 carbon atoms, an alkyl group having 1 to 6 carbon atoms, a straight or branched haloalkyl group having 1 to 6 carbon atoms, a phenyloxy group, a phenyloxy group substituted by a chlorine atom, an iodine atom, a bromine atom or a fluorine atom, an aralkyloxy group, an aralkyloxy group substituted by a chlorine atom, an iodine atom, a bromine atom or a fluorine atom, a straight or branched alkylamino group having 1 to 6 carbon atoms, a straight or branched haloalkoxy group having 1 to 6 carbon atoms and having a chlorine atom, an iodine atom, a bromine atom or a fluorine atom, a straight or branched alkylsulfonyl group having 1 to 6 carbon atoms and a straight or branched alkylthio group having 1 to 6 carbon atoms.

4. The compound according to claim 2, wherein the substituent for Ar is selected from the group consisting of a chlorine atom, a bromine atom, a fluorine atom, an alkoxy group having 1 to 4 carbon atoms, an alkyl group having 1 to 4 carbon atoms, a straight or branched haloalkyl group having 1 to 4 carbon atoms, a phenyloxy group, a phenyloxy group substituted by a chlorine atom, an iodine atom, a bromine atom or a fluorine atom, an aralkyloxy group, an aralkyloxy group substituted by a chlorine atom, an iodine atom, or a fluorine atom, a straight or branched alkylamino group having 1 to 4 carbon atoms, a straight or branched haloalkoxy group having 1 to 4 carbon atoms and having a chlorine atom, an iodine atom, a bromine atom or a fluorine atom, a straight or branched alkylsulfonyl group having 1 to 4 carbon atoms and a straight or branched alkylthio group having 1 to 4 carbon atoms.

5. The compound according to claim 2, wherein the substituent for Ar is selected from the group consisting of a chlorine atom, bromine atom, fluorine atom, methoxy group, trifluoromethyl group, 4-fluorophenoxy group, phenoxy group, benzyloxy group, phenethyloxy group, phenylpropyloxy group, dimethylamino group, trifluoromethoxy group, 2-chloro-1,1,2-trifluoroethoxy group, methanesulfonyl group and a methylthio group.

6. The compound according to claim 5, wherein R is a hydrogen atom or methyl group.

7. The compound according to claim 1, wherein the compound is represented by the formula (I''):

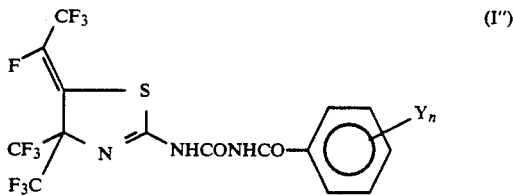

wherein Y represents a halogen atom, an alkyl group having 1 to 6 carbon atoms, an alkoxy group having 1 to 6 carbon atoms, a haloalkyl group having 1 to 6 carbon atoms, a haloalkoxy group having 1 to 6 carbon atoms, a nitro group, an acetyl group or a cyano group and n represents an integer of 0 to 5 or n=2 and $Y_n$ represents an unsaturated 6-membered ring formed with carbon atoms to which the Ys are bonded and the 6-membered ring is fused to the benzene ring.

8. The compound according to claim 7, wherein Y is at least one selected from the group consisting of a chlorine atom, bromine atom, fluorine atom, alkyl group having 1 to 6 carbon atoms, straight or branched alkoxy group having 1 to 6 carbon atoms, straight or branched haloalkyl group having 1 to 6 carbon atoms and having a chlorine atom, iodine atom, bromine atom or fluorine atom and a straight or branched haloalkoxy group having 1 to 6 carbon atoms and having a chlorine atom, iodine atom, bromine atom or fluorine atom.

9. The compound according to claim 7, wherein Y is at least one selected from the group consisting of a chlorine atom, bromine atom, fluorine atom, alkyl group having 1 to 4 carbon atoms, straight or branched alkoxy group having 1 to 4 carbon atoms, straight or branched haloalkyl group having 1 to 4 carbon atoms and having a chlorine atom, iodine atom, bromine atom or fluorine atom, and a straight or branched haloalkoxy group having 1 to 4 carbon atoms and having a chlorine atom, iodine atom, bromine atom or fluorine atom.

10. The compound according to claim 7, wherein Y is at least one selected from the group consisting of a chlorine atom, bromine atom, fluorine atom, methyl group, methoxy group, a trifluoromethyl group and trifluoromethoxy group.

11. The compound according to claim 10, wherein n is an integer of 1 or 2.

12. The compound according to claim 1, wherein the compound is selected from the group consisting of:
2-(2,6-difluorobenzoylamino)-4,4-bis(trifluoromethyl)-5-(tetrafluoroethylidene)-2-thiazoline,
2-(4-chlorobenzoylamino)-4,4-bis(trifluoromethyl)-5-(tetrafluoroethylidene)-2-thiazoline,
2-(3-chlorobenzoylamino)-4,4-bis(trifluoromethyl)-5-(tetrafluoroethylidene)-2-thiazoline,
2-(3,5-dichlorobenzoylamino)-4,4-bis(trifluoromethyl)-5-(tetrafluoroethylidene)-2-thiazoline,
2-(3,4-dichlorobenzoylamino)-4,4-bis(trifluoromethyl)-5-(tetrafluoroethylidene)-2-thiazoline,
2-(3-trifluoromethylbenzoylamino)-4,4-bis(trifluoromethyl)-5-(tetrafluoroethylidene)-2-thiazoline,
2-(3-nitrobenzoylamino)-4,4-bis(trifluoromethyl)-5-(tetrafluoroethylidene)-2-thiazoline,
2-(4-trifluoromethylbenzoylamino)-4,4-bis(trifluoromethyl)-5-(tetrafluoroethylidene)-2-thiazoline,
2-(3-fluorobenzoylamino)-4,4-bis(trifluoromethyl)-5-(tetrafluoroethylidene)-2-thiazoline,
2-(2,4-dichlorobenzoylamino)-4,4-bis(trifluoromethyl)-5-(tetrafluoroethylidene)-2-thiazoline,
2-(4-cyanobenzoylamino)-4,4-bis(trifluoromethyl)-5-(tetrafluoroethylidene)-2-thiazoline,
2-(4-fluorobenzoylamino)-4,4-bis(trifluoromethyl)-5-(tetrafluoroethylidene)-2-thiazoline,
2-(3-bromobenzoylamino)-4,4-bis(trifluoromethyl)-5-(tetrafluoroethylidene)-2-thiazoline,
2-(4-trifluoromethoxybenzoylamino)-4,4-bis(trifluoromethyl)-5-(tetrafluoroethylidene)-2-thiazoline,
2-(4-fluoro-3-trifluoromethylbenzoylamino)-4,4-bis(trifluoromethyl)-5-(tetrafluoroethylidene)-2-thiazoline,
2-(3-trifluoromethoxybenzoylamino)-4,4-bis(trifluoromethyl)-5-(tetrafluoroethylidene)-2-thiazoline,
N-[4,4-bis(trifluoromethyl)-5-(tetrafluoroethylidene)-2-thiazolin-2-yl] 4-trifluoromethylbenzenethioamide,
2-(3,4-difluorobenzoylamino)-4,4-bis(trifluoromethyl)-5-(tetrafluoroethylidene)-2-thiazoline, 2-{4-(2-chloro-1,1,2-trifluoroethoxy)benzoylamino}-4,4-bis(trifluoromethyl)-5-(tetrafluoroethylidene)-2-thiazoline,
2-(2-chloro-4-nitrobenzoylamino)-4,4-bis(trifluoromethyl)-5-(tetrafluoroethylidene)-2-thiazoline,
1-[4,4-bis(trifluoromethyl)-5-(tetrafluoroethylidene)-2-thiazolin-2-yl]-3-(2,6-dichlorobenzoyl)urea,
1-[4,4-bis(trifluoromethyl)-5-(tetrafluoroethylidene)-2-thiazolin-2-yl]-3-(2,6-difluorobenzoyl)urea,
1-[4,4-bis(trifluoromethyl)-5-(tetrafluoroethylidene)-2-thiazolin-2-yl]-3-(2-chlorobenzoyl)urea,
1-[4,4-bis(trifluoromethyl)-5-(tetrafluoroethylidene)-2-thiazolin-2-yl]-3-(2-fluorobenzoyl)urea,
1-[4,4-bis(trifluoromethyl)-5-(tetrafluoroethylidene)-2-thiazolin-2-yl]-3-(2-methylbenzoyl)urea,
1-[4,4-bis(trifluoromethyl)-5-(tetrafluoroethylidene)-2-thiazolin-2-yl]-3-(2,4-dichlorobenzoyl)urea,
1-[4,4-bis(trifluoromethyl)-5-(tetrafluoroethylidene)-2-thiazolin-2-yl]-3-(2-chloro-4-nitrobenzoyl)urea,
1-[4,4-bis(trifluoromethyl)-5-(tetrafluoroethylidene)-2-thiazolin-2-yl]-3-(2,4-difluorobenzoyl)urea,
1-[4,4-bis(trifluoromethyl)-5-(tetrafluoroethylidene)-2-thiazolin-2-yl]-3-(2-trifluoromethylbenzoyl)urea,
1-[4,4-bis(trifluoromethyl)-5-(tetrafluoroethylidene)-2-thiazolin-2-yl]-3-(2,4,6-trichlorobenzoyl)urea,
1-[4,4-bis(trifluoromethyl)-5-(tetrafluoroethylidene)-2-thiazolin-2-yl]-3-(2-bromobenzoyl)urea,
1-[4,4-bis(trifluoromethyl)-5-(tetrafluoroethylidene)-2-thiazolin-2-yl]-3-(2,3-dichlorobenzoyl)urea and
1-[4,4-bis(trifluoromethyl)-5-(tetrafluoroethylidene)-2-thiazolin-2-yl]-3-(2-chloro-6-fluorobenzoyl)urea.

13. The compound according to claim 1, wherein the compound is selected from the group consisting of:
2-(2,6-difluorobenzoylamino)-4,4-bis(trifluoromethyl)-5-(tetrafluoroethylidene)-2-thiazoline,
2-(4-chlorobenzoylamino)-4,4-bis(trifluoromethyl)-5-(tetrafluoroethylidene)-2-thiazoline,
2-(3-chlorobenzoylamino)-4,4-bis(trifluoromethyl)-5-(tetrafluoroethylidene)-2-thiazoline,
2-(3,5-dichlorobenzoylamino)-4,4-bis(trifluoromethyl)-5-(tetrafluoroethylidene)-2-thiazoline,
2-(3,4-dichlorobenzoylamino)-4,4-bis(trifluoromethyl)-5-(tetrafluoroethylidene)-2-thiazoline,
2-(3-trifluoromethylbenzoylamino)-4,4-bis(trifluoromethyl)-5-(tetrafluoroethylidene)-2-thiazoline,
2-(3-nitrobenzoylamino)-4,4-bis(trifluoromethyl)-5-(tetrafluoroethylidene)-2-thiazoline,
2-(4-trifluoromethylbenzoylamino)-4,4-bis(trifluoromethyl)-5-(tetrafluoroethylidene)-2-thiazoline,
2-(3-fluorobenzoylamino)-4,4-bis(trifluoromethyl)-5-(tetrafluoroethylidene)-2-thiazoline,
2-(2,4-dichlorobenzoylamino)-4,4-bis(trifluoromethyl)-5-(tetrafluoroethylidene)-2-thiazoline,
2-(4-cyanobenzoylamino)-4,4-bis(trifluoromethyl)-5-(tetrafluoroethylidene)-2-thiazoline,
2-(4-fluorobenzoylamino)-4,4-bis(trifluoromethyl)-5-(tetrafluoroethylidene)-2-thiazoline,
2-(3-bromobenzoylamino)-4,4-bis(trifluoromethyl)-5-(tetrafluoroethylidene)-2-thiazoline,
2-(4-trifluoromethoxybenzoylamino)-4,4-bis(trifluoromethyl)-5-(tetrafluoroethylidene)-2-thiazoline,
2-(4-fluoro-3-trifluoromethylbenzoylamino)-4,4-bis(trifluoromethyl)-5-(tetrafluoroethylidene)-2-thiazoline,
2-(3-trifluoromethoxybenzoylamino)-4,4-bis(trifluoromethyl)-5-(tetrafluoroethylidene)-2-thiazoline,
2-(3,4-difluorobenzoylamino)-4,4-bis(trifluoromethyl)-5-(tetrafluoroethylidene)-2-thiazoline,
2-(2-chloro-4-nitrobenzoylamino)-4,4-bis(trifluoromethyl)-5-(tetrafluoroethylidene)-2-thiazoline,
1-[4,4-bis(trifluoromethyl)-5-(tetrafluoroethylidene)-2-thiazolin-2-yl]-3-(2,6-difluorobenzoyl)urea,
1-[4,4-bis(trifluoromethyl)-5-(tetrafluoroethylidene)-2-thiazolin-2-yl]-3-(2-chlorobenzoyl)urea,
1-[4,4-bis(trifluoromethyl)-5-(tetrafluoroethylidene)-2-thiazolin-2-yl]-3-(2-fluorobenzoyl)urea,
1-[4,4-bis(trifluoromethyl)-5-(tetrafluoroethylidene)-2-thiazolin-2-yl]-3-(2-methylbenzoyl)urea and
1-[4,4-bis(trifluoromethyl)-5-(tetrafluoroethylidene)-2-thiazolin-2-yl]-3-(2-chloro-6-fluorobenzoyl)urea.

14. An insecticidal, acaricidal or fungicidal composition which comprises a thiazoline derivative represented by the formula (I) as claimed in claim 1 as an effective ingredient and a carrier.

* * * * *

UNITED STATES PATENT AND TRADEMARK OFFICE
CERTIFICATE OF CORRECTION

PATENT NO. : 5,221,685
DATED : June 22, 1993
INVENTOR(S) : Tokio Obata et al.

It is certified that error appears in the above-indentified patent and that said Letters Patent is hereby corrected as shown below:

Claim 1, column 34, line 9, change "an alkoxy" to --a haloalkyl--.

Claim 2, column 34, line 38, change "a lower alkyl group" to --an alkyl group--.

Signed and Sealed this

Thirteenth Day of September, 1994

Attest:

BRUCE LEHMAN

Attesting Officer  Commissioner of Patents and Trademarks